United States Patent

Mattsson-Boze et al.

[11] Patent Number: 6,097,423
[45] Date of Patent: Aug. 1, 2000

[54] IMAGE ORIENTATION FOR ENDOSCOPIC VIDEO DISPLAYS

[75] Inventors: Daniel Mattsson-Boze, Goleta; David Chatenever, Santa Barbara, both of Calif.

[73] Assignee: Karl Storz Imaging, Inc., Goleta, Calif.

[21] Appl. No.: 08/870,792

[22] Filed: Jun. 6, 1997

[51] Int. Cl.[7] .................................................. A62B 1/04
[52] U.S. Cl. ............................. 348/65; 348/66; 348/67; 356/241; 128/4
[58] Field of Search .............................. 348/65, 66, 68, 348/69, 70, 75, 82; 358/42, 98, 99; 128/777; 356/4, 241; 385/117; A62B 1/04

[56] References Cited

U.S. PATENT DOCUMENTS

| 4,816,909 | 3/1989 | Kimura et al. ........................... 358/98 |
| 4,875,091 | 10/1989 | Yamada et al. ........................... 358/42 |
| 4,891,697 | 1/1990 | Saito et al. ............................... 358/98 |
| 4,951,135 | 8/1990 | Sasagawa et al. ....................... 358/98 |
| 5,408,265 | 4/1995 | Sasaki ...................................... 348/70 |
| 5,518,008 | 5/1996 | Cuuchiaro ............................... 128/777 |

*Primary Examiner*—Howard Britton
*Assistant Examiner*—Tung Vo
*Attorney, Agent, or Firm*—St. Onge Steward Johnston & Reens LLC

[57] ABSTRACT

An endoscope and camera are described with which a display observed through the optics in the endoscope is rotated to a desired orientation using an accelerometer. The accelerometer generates a signal indicative of the local vertical and is used in the particular embodiment to rotate a CCD image sensor aligned with the optical axis of the endoscope so as to maintain a desired orientation of a display of the image on a monitor.

6 Claims, 2 Drawing Sheets

IMAGE ORIENTATION FOR ENDOSCOPIC VIDEO DISPLAYS

FIELD OF THE INVENTION

Video displays of images obtained from an endoscope, in which the rotational orientation of the image as viewed on the screen is presented in its actual relationship to the viewer's reference frame.

BACKGROUND OF THE INVENTION

An endoscope is an elongated tubular structure which is inserted into body cavities to examine them. The endoscope includes a telescope with an objective lens at its distal end. The telescope includes an image-forwarding system. In rigid endoscopes it is a series of spaced-apart lenses. In flexible endoscopes it is a bundle of tiny optical fibers assembled coherently to forward the image. This invention is applicable to both types of image forwarding systems.

At the proximal end of the image-forwarding system is an ocular lens which creates a virtual image for direct human visualization. Often a camera means such as a CCD chip, is mounted to the endoscope. It receives the image and produces a signal for a video display.

While surgeons can, and often do, look directly into the endoscope through an ocular lens, it is more common for them to use an attached video camera and observe an image on a video screen. In a surgical or diagnostic procedure, the surgeon manipulates the endoscope. He may tilt it, push it in, pull it out, and also rotate it around its mechanical axis. As these manipulations occur to an endoscope with an attached CCD camera, the camera faithfully relates what it sees, with its own upright axis displayed as the upright axis of the image on the display. This means that if the camera is rigidly fixed to the endoscope, then as the endoscope-camera is rotated around its mechanical axis, the displayed image on the monitor will move proportionately and in the opposite direction as the endoscope-camera. A clockwise rotation of the endoscope-camera through an angle of 45 degrees will cause a counterclockwise rotation of the image on the monitor through an angle of 45 degrees.

That is the very problem. When the image is displayed on the screen and the endoscope is rotated around its axis, it is as though the surgeon must tilt his head to follow it. However, the surgeon is standing up, and the rotating image is distracting to him. What he really wants to see on the screen is an image that is oriented the same as he would see it if he were inside, standing up, with the same upright orientation. Stated otherwise, he would prefer to see what he would see if he were looking directly into the endoscope, instead of viewing a screen. This is impossible when the camera is fixed to the telescope and rotates with it, while the surgeon does not.

In a conventional endoscope and camera arrangement, the camera is usually detachably and rotably connected to the endoscope. In this arrangement the rotated image on the monitor screen can be righted by manually counter-rotating only the camera such that its orientation is upright. Alternatively, one can avoid this rotated image condition by holding the camera in its upright position and rotating only the endoscope.

Suggestions have been made to decouple the camera from the telescope so the camera can rotate independently of it, using a pendulum to seek the vertical. This seemingly sensible approach runs afoul of conditions imposed by the use of the instrument. Endoscopes are used in close quarters, and their proximal ends must be kept as small and uncluttered as possible. Physical interference with surroundings and with the surgeon's hands must be eliminated or greatly minimized. However, a pendulum to be useful must have a substantial mass and a substantial arc to work through, requiring enlargement of the instrument. Furthermore, when the endoscope is tilted, the axis of rotation of the pendulum is no longer horizontal. Now there must be bearings to support the pendulum, and the component of the force of gravity acting on the pendulum is reduced. Even worse, when the slope is very steep, a mechanical pendulum may not receive a sufficient force to seek the vertical.

Sometimes, however, there may be reasons to attach the endoscope such that it cannot rotate with respect to the camera. Or, alternatively, it may be desirable to embed the CCD camera within the endoscope housing. In these circumstances it is not possible to manually rotate the camera with respect to the endoscope, so some other means is necessary to right the displayed image. Furthermore it is desirable to have this image rotation occur automatically so that, regardless of the physical orientation of the endoscope-camera in space, the displayed image of an object will always be correctly oriented with respect to the viewer's reference frame.

Rotation of the image by electronic manipulation would appear to be a useful solution. However, it runs afoul of the aspect ratio of the camera and of its display. Such rotation can eliminate from the display information located near corners and edges of the viewed field which might be of interest to the surgeon. This problem can be visualized by rotating a photograph in a picture frame. Also, this requires exotic and expensive attitude sensing devices.

It is an object of this invention to maintain the rotary position of the CCD image sensing device so that its upright axis lies in a vertical plane with respect to the viewer utilizing an accelerometer responsive to gravity, a servo mechanism responsive to its signal, and a servo motor to rotate the CCD sensing device.

BRIEF DESCRIPTION OF THE INVENTION

An endoscopic camera system includes a camera head which has an internal image sensing device (such as a CCD sensor), a camera control unit which processes the signals from the camera head into a standard video signal (such as NTSC) suitable for inputing to a standard television monitor, and a video display to display the image received by the camera from an endoscope. The CCD sensor is rotatably mounted to the camera head frame so that its central axis is coincident with that of the optical input to the camera head.

According to a feature of this invention an accelerometer responsive to the force of gravity is fixed to the CCD. The accelerometer produces a signal proportional to its position relative to vertical in standard gravitational field. The signal is at its maximum when its upright axis is vertical. Servo means is provided to maximize this signal by causing a servo motor to rotate the CCD so as to maintain the maximum value. With this arrangement the view presented by the video display will always be "level", as though viewed by a surgeon standing or sitting in an upright position.

The above and other features of this invention will be fully understood from the following detailed description and the accompanying drawings, in which:

DETAILED DESCRIPTION OF THE INVENTION

Figure 1:
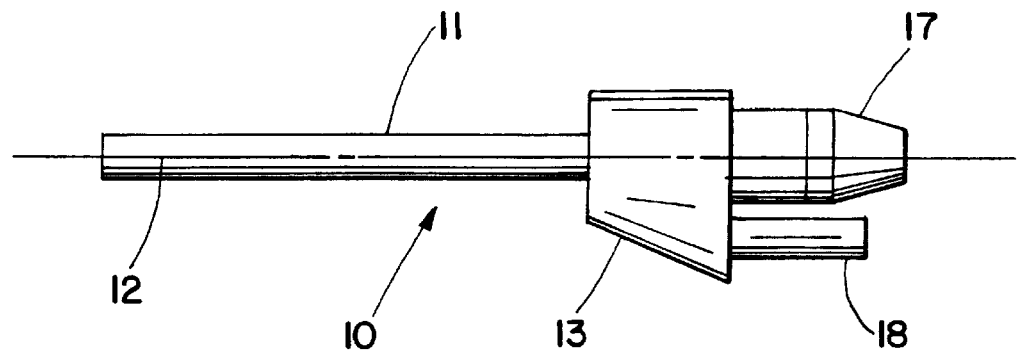
FIG. 1 is a side view of an endoscope useful with this invention.

FIG. 1 schematically shows an endoscope 10. The endoscope includes a shaft 11 that contains elements that are conventionally provided. An image-forwarding system such as a series of lenses or a coherent fiber optic bundle, a light guide, and instrument channels are examples. They are not shown in detail because it is not necessary for an understanding of this invention. The image forwarding system has a central optical axis 12. The endoscope may be permanently or releasably attached to a fitting 13.

The fitting is releasably attachable to a frame 14. The frame 14 itself has a lateral axis 15 which is horizontal when the frame is in its upright position, and an upright axis 16 which is vertical in the gravitational field when the frame is in its upright position. Axes 15 and 16 are normal to each other.

Figure 2:
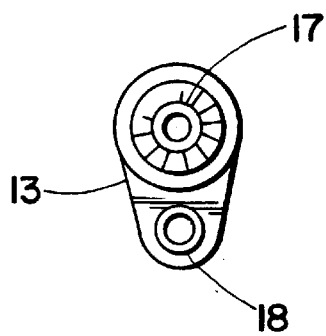
FIG. 2 is a right hand end view of FIG. 1.
Figure 3:
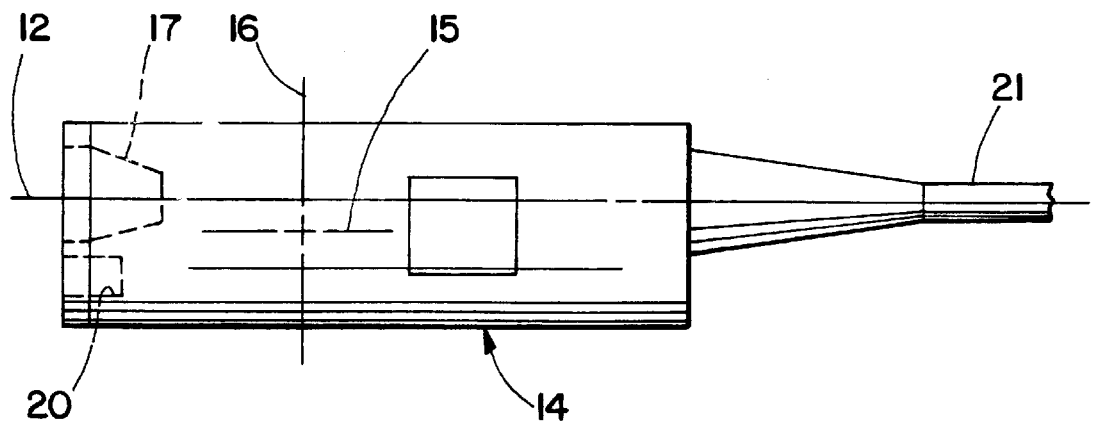
FIG. 3 is a side view, partly in schematic notation showing a frame for the image-capturing and orienting portions of this invention, and for mounting the endoscope.
Figure 4:
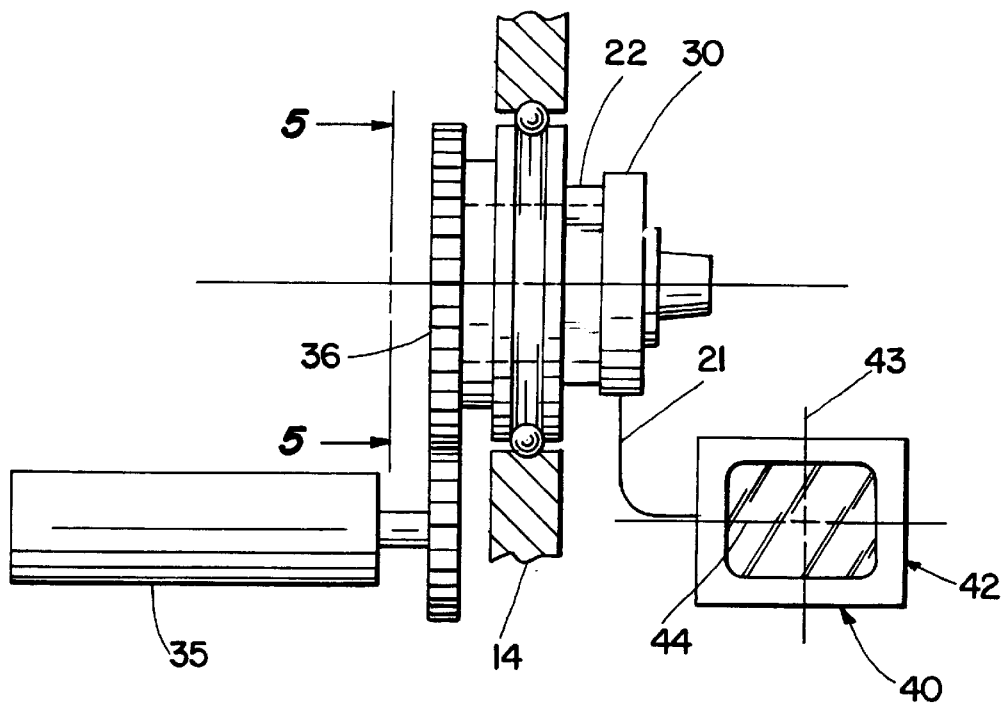
FIG. 4 is a side view of the image-capturing and orienting portions of the invention.
Figure 5:
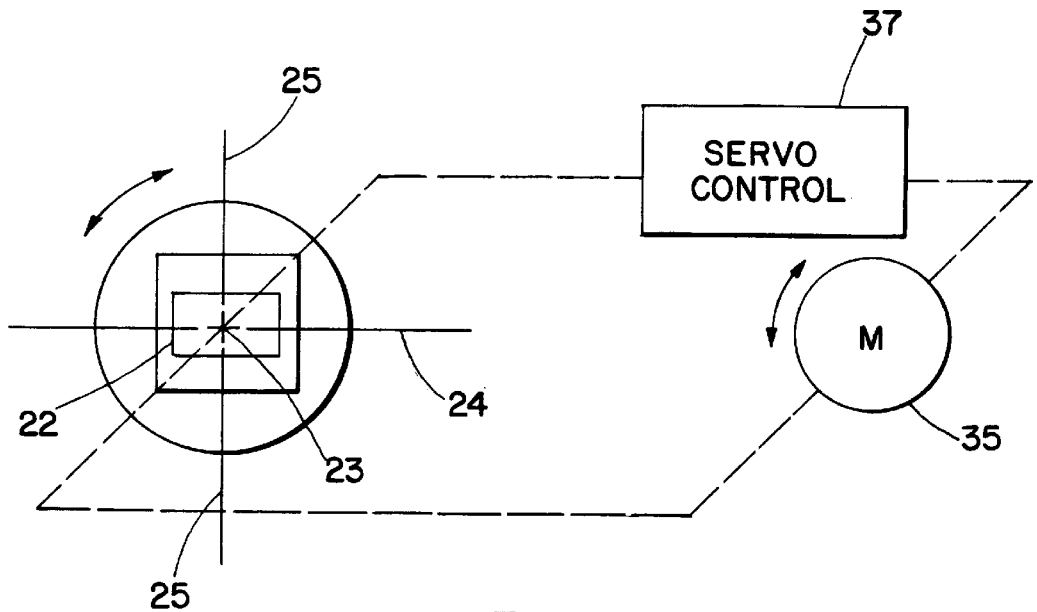
FIG. 5 is a schematic diagram illustrating the control system of the invention.

As shown in FIGS. 1–3, fitting 13 carries two prongs 17, 18 that respectively are plugged into receptacles 19, 20 in frame 14. Prong 17 is the culmination of the image path through the endoscope. It may be directly in line with it, or may be offset with the use of prisms, mirrors or other means to displace the optical axis 12 laterally. When the endoscope is properly fitted to the frame, the image is conducted into the frame, as will be seen. This is an example of a construction wherein the endoscope cannot be rotated relative to the frame in which the camera is mounted. If the image is to be maintained "upright", then the camera must itself be rotated.

Prong 18 receives light for illumination from a source not shown, but which may be transmitted to it through a fiber optic cable that may be part of cable 21, connected to the frame. If preferred, a separate light cable can be provided and attached to the frame as appropriate. This prong arrangement assures correct alignment of the endoscope relative to the frame.

A CCD chip 22 (sometimes called a "camera") is rotatably mounted to the frame. Its center point 23 is located on the optical axis of the optical system. The camera is rotatable around the optical axis, relative to the optical system and to the frame. The camera has its own lateral axis 24 and upright axis 25.

An accelerometer 30 is also rotatably mounted to the frame, and is intended to rotate with the camera. Most conveniently, the accelerometer is directly bonded to the CCD. Both are rotatively journaled to the frame. When they are bonded together, a single bearing 31 can serve to journal both of them.

The accelerometer is capable of sensitively responding to variations in the components of gravitational force to which it is exposed. Integrated accelerometers of the type used in air bags are suitable for this purpose. Analog Devices ADXL-05, which includes a micro-machined silicon cantilever suspended between two electrodes, is an example of an appropriate accelerometer. An AC signal can be imposed on the two electrodes, and the detected proximity of the cantilever to the two electrodes will provide for a servo signal respective to off-vertical orientation.

Here it will be noted that the endoscope when in use will have freedom to tilt in all directions, so that the accelerometer will often be responding to a component of vertical gravitational force which is considerably less than its maximum value. For example, when the optical axis is depressed 60 degrees, the vertical component of gravity to which the accelerometer refers while keeping the image upright is much less than maximum gravity force. It is an advantage of this device, which a pendulum does not share, that it can respond properly over a large angular range in which the vertical component of gravity is quite small.

A bi-directional servo motor 35 is drivingly connected to the camera and to the accelerometer by a gear train 36. It responds to the signal from a servo control 37 to rotate the camera and the accelerometer so the accelerometer will produce a maximum signal. That is, the largest signal relative to signals which would be generated by rotating the accelerometer in either direction. The servo control generates its signal in response to accelerator output.

The camera provides its signal to a video display 40 through leads in cable 21. This display will ordinarily be placed on a shelf or be held by a bracket on a wall or a ceiling. Its screen 42 has an upright axis 43 and a lateral axis 44. These axes will generally be viewed as vertical and horizontal. If the camera is maintained upright, then the display axes will coincide with the camera axes. It will now be seen that rotating the CCD to maintain its axes in a nominally horizontal and vertical alignment will provide the same orientation to the image on the screen whatever the position of the endoscope may be. As a consequence, the surgeon will remain spatially oriented relative to the operating site. He need not exert efforts to orient himself relative to an image that rotates on the display.

As a further advantage, this arrangement displays the full area of the field available from the camera. The aspect ratio of the screen and of the camera are the same. If the image were rotated, corners and some of the edges of the screen would be blank. Possibly important information from the corners of the camera could be lost. This invention does not suffer this risk.

This invention is not to be limited by the embodiment shown in the drawings and described in the description, which is given by way of example and not of limitation, but only in accordance with the scope of the appended claims.

We claim:

1. In an endoscope having a frame, an optical forwarding system, and a camera, said optical system having a central optical axis and forming relative to said frame an image with an upright axis and a lateral axis, said camera having a sensitive area centered on said central optical axis, and having relative to itself an upright axis and a lateral axis, the improvement comprising:

an accelerometer responsive to the force of gravity;

means mounting said accelerometer and camera to said frame for simultaneous rotation around said optical axis;

bi-directional motor means adapted to rotate said camera and said accelerometer around said central optical axis; and servo control means responsive to a signal from said accelerometer to cause said motor to rotate said camera and accelerometer to seek to position said camera so its upright axis will be in a vertical plane that includes said central optical axis;

whereby, when an image derived from said camera is displayed on a video display, the lateral axis of the image will coincide with the horizontally disposed lateral axis of the video display.

2. Apparatus according to claim 1 in which said camera is a CCD chip.

3. Apparatus according to claim 2 in which said accelerometer is bonded to said chip.

4. Apparatus according to claim 1 in which said camera is a video camera.

5. Apparatus according to claim 1 in which said accelerometer includes a silicon cantilever positioned between a pair of electrodes, its location relative to said electrodes providing said signal to said servo control.

6. In an endoscope having a frame, an optical forwarding system and a camera to record images passed through said optical forwarding system, said optical system having a central optical axis and forming, relative to said frame, an optical image, said camera having a light sensitive area operatively aligned with respect to said optical axis to produce an output image representative of the optical image, and a display for said output image, the improvement comprising:

an accelerometer producing an accelerometer signal indicative of a local vertical, an image rotator responsive to said accelerometer signal to effectively rotate the displayed output image to a desired orientation relative to the local vertical.

\* \* \* \* \*